United States Patent [19]

Person et al.

[11] Patent Number: 5,807,349

[45] Date of Patent: Sep. 15, 1998

[54] CATHETER HAVING VALVE MECHANISM

[75] Inventors: Wayne C. Person, Newtown; Dominick L. Mastri, Bridgeport; William J. Vumback, Northford; Patrick D. Mozdzierz, Bridgeport, all of Conn.

[73] Assignee: United States Surgical Corporation, Norwalk, Conn.

[21] Appl. No.: 813,935

[22] Filed: Mar. 10, 1997

[51] Int. Cl.⁶ ........................................................ A61M 5/00
[52] U.S. Cl. ............................................ 604/247; 604/280
[58] Field of Search ..................................... 604/246, 247, 604/248, 264, 280, 281–284

[56] References Cited

U.S. PATENT DOCUMENTS

| | | |
|---|---|---|
| Re. 31,873 | 4/1985 | Howes . |
| 2,393,003 | 1/1946 | Smith . |
| 3,020,913 | 2/1962 | Heyer . |
| 3,128,769 | 4/1964 | Scislowicz . |
| 3,308,819 | 3/1967 | Arp . |
| 3,885,561 | 5/1975 | Cami . |
| 3,888,249 | 6/1975 | Howes . |
| 4,214,593 | 7/1980 | Imbruce et al. . |
| 4,434,810 | 3/1984 | Atkinson . |
| 4,475,898 | 10/1984 | Brodner et al. . |
| 4,529,399 | 7/1985 | Groshong et al. . |
| 4,549,879 | 10/1985 | Groshong et al. . |
| 4,559,046 | 12/1985 | Groshong et al. . |
| 4,671,796 | 6/1987 | Groshong et al. . |
| 4,701,166 | 10/1987 | Groshong et al. . |
| 4,753,640 | 6/1988 | Nichols et al. . |
| 4,801,297 | 1/1989 | Mueller . |
| 4,973,319 | 11/1990 | Melsky . |
| 4,995,863 | 2/1991 | Nichols et al. . |
| 5,030,210 | 7/1991 | Alchas . |
| 5,057,080 | 10/1991 | Takahashi . |
| 5,147,332 | 9/1992 | Moorehead . |
| 5,156,600 | 10/1992 | Young . |
| 5,160,325 | 11/1992 | Nichols et al. . |
| 5,207,655 | 5/1993 | Sheridan . |
| 5,224,938 | 7/1993 | Fenton, Jr. . |
| 5,250,037 | 10/1993 | Appling et al. . |
| 5,261,885 | 11/1993 | Lui . |
| 5,267,979 | 12/1993 | Appling et al. . |
| 5,304,155 | 4/1994 | Lui . |
| 5,391,148 | 2/1995 | Bonis . |
| 5,460,618 | 10/1995 | Harreld . |
| 5,522,807 | 6/1996 | Luther . |
| 5,531,679 | 7/1996 | Schulman et al. . |
| 5,554,136 | 9/1996 | Luther . |
| 5,556,390 | 9/1996 | Hicks . |

*Primary Examiner*—John D. Yasko

[57] ABSTRACT

An improved catheter having a closed distal end and a valve adjacent the distal end which communicates the lumen of the catheter with the exterior of the catheter to permit the infusion or aspiration of fluids between the catheter and the vessel in which the catheter is positioned. The valve is preferably in a plane which is oriented at an angle to the longitudinal axis of the catheter, and is preferably in an area of reduced wall thickness to facilitate opening and closing.

23 Claims, 7 Drawing Sheets

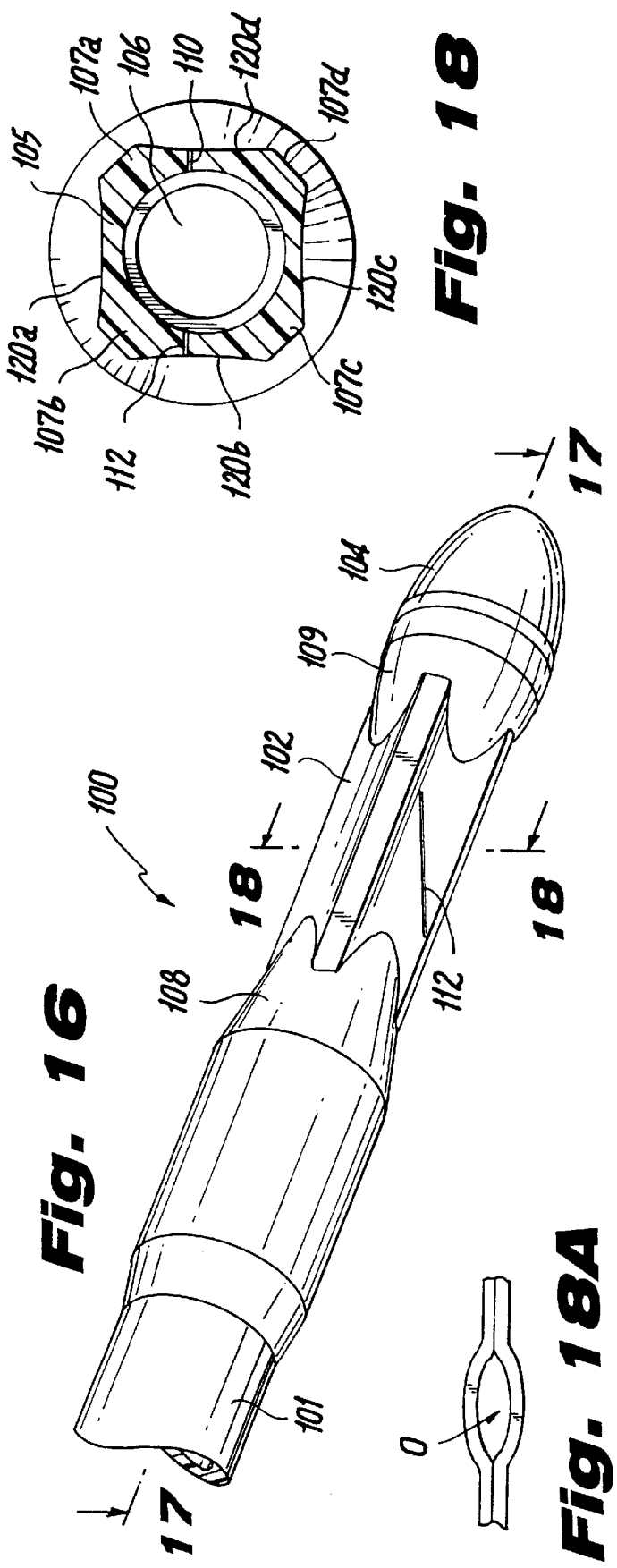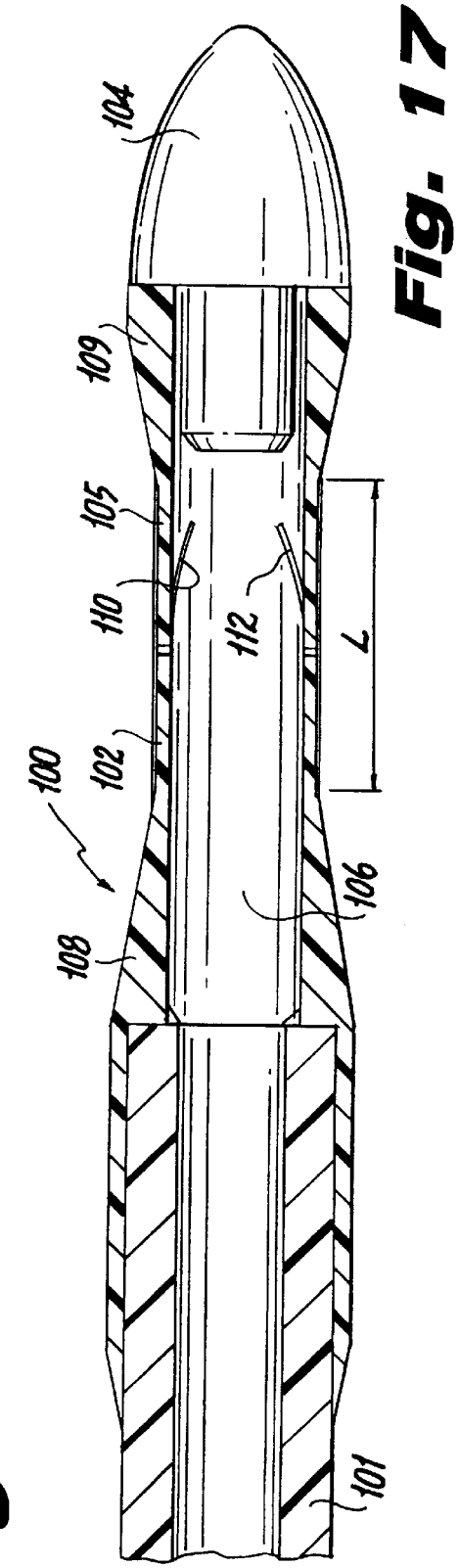

CATHETER HAVING VALVE MECHANISM

BACKGROUND

1. Technical Field

This application relates in general to catheters having slit valves to permit ingress and egress of fluids through the catheter into and out of the body of a patient.

2. Discussion of the Prior Art

The use of catheters in intravenous procedures and for intravenous therapies is well known in the medical community. Catheters typically are implanted into various vessels in the patient's body to provide for the ingress and/or egress of fluids, such as blood and other bodily fluids, and as well for the infusion of medication or other medical solutions for both specific treatment of the patient and to facilitate other treatments and diagnoses. The use of catheters may be for short term procedures, and are also commonly used in long term procedures wherein the catheter is implanted in the body and left in place for an extended period of time to facilitate long term treatment of the patient.

Catheters typically take the form of an elongated tube constructed of a biocompatible surgical grade material which is flexible to permit guiding or steering of the catheter through blood vessels or anatomical passages. Initially, catheters generally included an open ended tube which was positioned during the surgical procedure, and was capped at its proximal end (i.e., the end positioned outside the body) to provide a port for the infusion or withdrawal of fluids. The distal end of the catheter remained open inside the vessel within the patient's body, and allowed for ready withdrawal or infusion of fluids through the catheter. These catheters were typically used in short term procedures, such as surgical procedures in which the catheter would be removed after completion of the surgical procedure. Leaving a catheter of the open-ended type in the vessel of the patient subjected the catheter to a number of potential problems, including the formation of blood clots which would obstruct the end of the catheter. Open-ended catheters are thus flushed regularly, typically with a saline and/or anticoagulant solution, to keep the distal end of the catheter open.

Catheters intended to remain in the body for a longer term have been developed and generally include a closed distal end and a valve adjacent the distal end to permit the infusion or withdrawal of fluids. Typically, these valves operate by reacting to the pressure differential within the tube as compared to the vessel (or other anatomical location) in which the catheter is placed. Generally, increasing the pressure within the catheter provides for infusion of fluids through the valve and into the vessel, while a pressure decrease in the catheter provides for withdrawal of the fluids from the site in which the catheter is placed.

A challenge associated with closed end catheters having valves adjacent their distal end is the performance of the valve based on a pressure differential. Although efforts have been made to optimize the performance of such valved catheters, e.g., by chemical weakening the are of the catheter tube adjacent to the valve or other localized treatment (see e.g., U.S. Pat. Nos. 4,549,879 and 4,701,166 to Groshong et al.; 4,995,863 to Nicholas et al.; and 5,147,332 to Moorehead), a need remains to further optimize the fabrication and/or performance of existing valved catheters.

SUMMARY

The present catheter device includes an elongated flexible tube which has an open end, a closed end and which is fabricated from a surgical grade material. The catheter tube has a wall which is defined by an inner and outer surface of the tube, where the inner surface of the tube is defined by a lumen which extends the length of the tube. In one preferred embodiment, when viewed in cross-section at two different longitudinal points, at least a portion of the tube at the more distal point has a reduced thickness with respect to the tube when viewed at a more proximal point, and at least one valve is positioned solely in the portion of reduced thickness so as to communicate the lumen with the exterior of the tube. The valve is oriented at an angle to the longitudinal axis of the tube.

The reduced thickness portion of the catheter tube, in a further embodiment, is the result of the lumen of the catheter tube being offset and parallel to the longitudinal axis of the tube, and in another embodiment is the result of the lumen having an oval cross-section such that the major axis of the oval defines the portions of reduced thickness in the wall of the tube. In each of these cases, the valve is provided in the portion or portions of reduced thickness, and does not extend into the areas of increased thickness so that the operation of the valve is consistent along its length.

In an alternate embodiment of the present catheter, the slit valves comprise at least one pair of slits which are parallel to each other but are positioned at an angle to the longitudinal axis of the catheter tube. Preferably, the slits, when formed through the tube, are cut at different angles relative to the catheter tube wall surface to facilitate the infusion or withdrawal of fluids.

In each of the embodiments, it is preferred that the valves are positioned at an angle to the longitudinal axis of the catheter in an area of reduced thickness to increase the size of the opening for the ingress and egress of fluids.

BRIEF DESCRIPTION OF THE DRAWINGS

The features of the present catheter will become apparent from the detailed description set forth below, taken with reference to the accompanying drawings, in which:

FIG. 16 is a perspective view of the present catheter according to a fifth embodiment;

FIG. 17 is a side cross-sectional view of the catheter of FIG. 16 taken along lines 17—17 of FIG. 16;

FIG. 18 is a cross-sectional view of the catheter of FIG. 16 taken along lines 18—18 of FIG. 16;

FIG. 18A illustrates a top view of the slit when opened during applications of suction;

DETAILED DESCRIPTION OF THE ILLUSTRATED EMBODIMENTS

Figure 1:
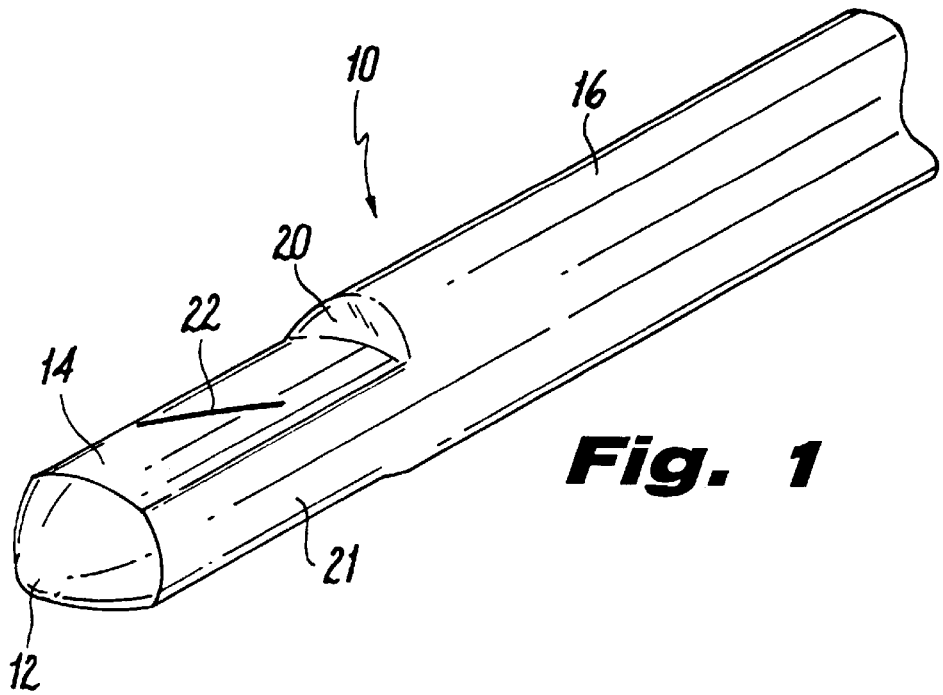
FIG. 1 is a perspective view of the present catheter according to a first embodiment.
Figure 2:
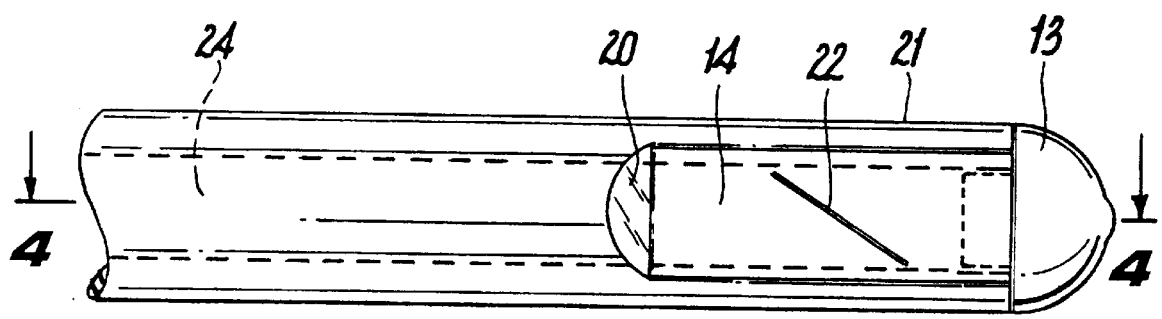
FIG. 2 is a top plan view of the present catheter of FIG. 1.
Figure 3:
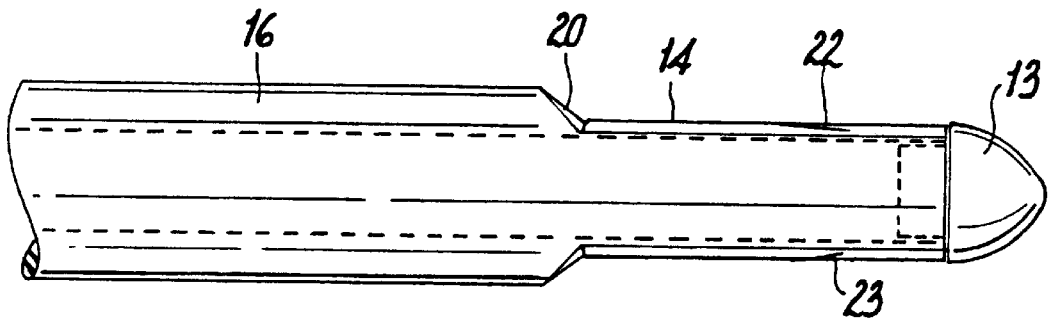
FIG. 3 is a side elevation view of the present catheter of FIG. 1.

Referring now to the drawings, in which like reference numerals represent similar or identical elements throughout the several views, there is illustrated in FIG. 1 the present catheter 10 having a valve 22 positioned in an area of reduced thickness relative to proximal portions of catheter 22 which in combination with its orientation discussed below, facilitates the operation of the valve to open and close for infusing or withdrawing fluids. Catheter 10 preferably is constructed of a flexible, biocompatible surgical grade material and terminates in closed distal end 12, which may take the form of an end cap 13, as seen in FIGS. 2–4, or may be molded as part of the catheter body 16.

Figure 4:
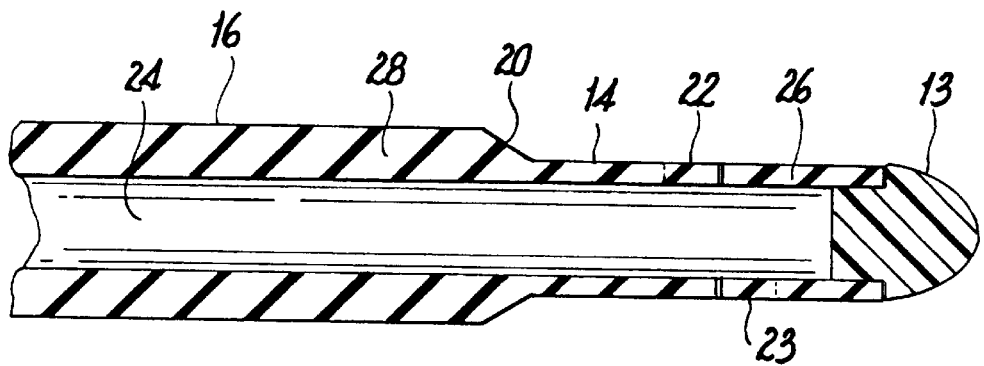
FIG. 4 is a side cross-sectional view of the catheter of FIG. 1 taken along lines 4—4 of FIG. 2.
Figure 5:
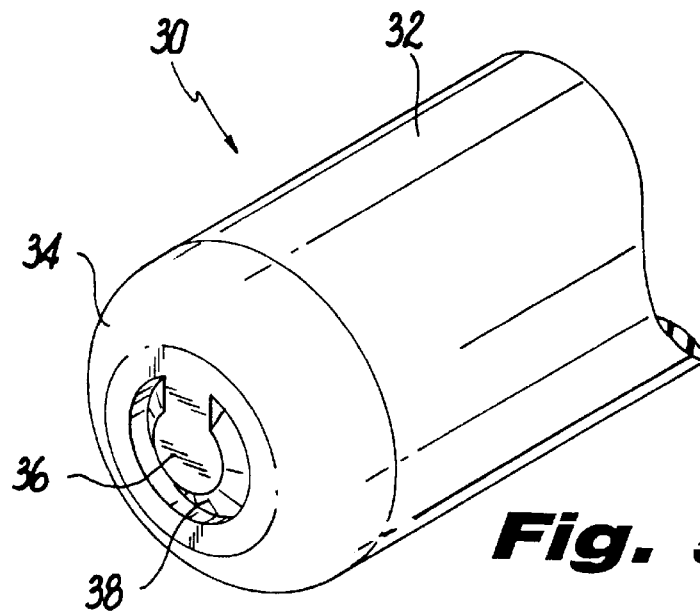
FIG. 5 is a perspective view of the present catheter according to a second embodiment.

Body 16 has a first diameter which corresponds to a first thickness 28, as seen in FIG. 4, of the wall of the catheter 10. A transition region 20 is provided which leads to a region 14, which is preferably substantially planar and which has a second reduced thickness 26 that is reduced relative to first thickness 28, as best seen in FIG. 4. The reduced thickness adds flexibility to the slit valves 22, 23 thereby facilitating opening and closing of the valves.

Slit valves 22, 23 open in response to increased or decreased pressure within the lumen 24 to permit infusion and egress of fluids into or from the catheter into the vessel in which the catheter is positioned. In the embodiment shown in FIGS. 3 and 4, a pair of slit valves 22, 23 are cut or otherwise configured in such a manner so as to provide for infusion through one valve, i.e. valve 22, and egress through a second valve, i.e. valve 23. That is, in this embodiment, valve 22 opens in response to increased pressure in lumen 24 and valve 23 opens in response to decreased pressure in lumen 24. Planar region 14 facilitates opening and closing of the valves through the reduced thickness 26 of the wall of the catheter, and it can be seen that valves are positioned exclusively within the area of reduced thickness 26. In an alternate embodiment, the slit valves 22, 23 are identical and the ingress and egress of fluids is through both valves.

Preferably, planar region 14 is formed in wall 28 on diametrically opposite sides of catheter 10. As seen in FIG. 4, however, the reduction in wall thickness does not impact on the diameter of lumen 24, which is maintained substantially constant throughout the length of catheter 10. As seen in FIG. 2, the outer diameter of the catheter 10 remains constant along sides 21. Alternately, the thickness of wall 28 can be reduced circumferentially about the end of catheter 10 distal of transition region 20, with the wall thickness being constant at this distal end of catheter 10 and the diameter of the lumen remaining constant throughout the catheter length.

FIGS. 1 and 2 show the valve 22 oriented at an angle to the longitudinal axis of catheter 10. Thus, valve 22 lies in a plane oriented at an angle to the longitudinal axis. Positioning the valve 22 at an angle within the reduced wall thickness results in a larger opening for the ingress and egress of fluids. When suction is applied, the reduced thickness wall will want to collapse so it will twist. Thus the slit opens into an eye-shaped opening as shown for example in FIG. 18A. A preferred angular orientation of valve 22 relative to the longitudinal axis is 30 degrees, although differing angles, and particularly greater angles, will provide the desired advantage.

FIGS. 5–8 illustrate a second embodiment of the present catheter 30, in which the reduced wall thickness 34 is located at the distalmost end of the catheter 30. Valve 36 is provided in the tapered closed distal end 34 and permits the infusion or egress of fluids in response to increased or decreased pressure, respectively, in the lumen of the catheter. Opening 38 permits the ingress or egress of fluids through the distal end 34.

Figure 6:
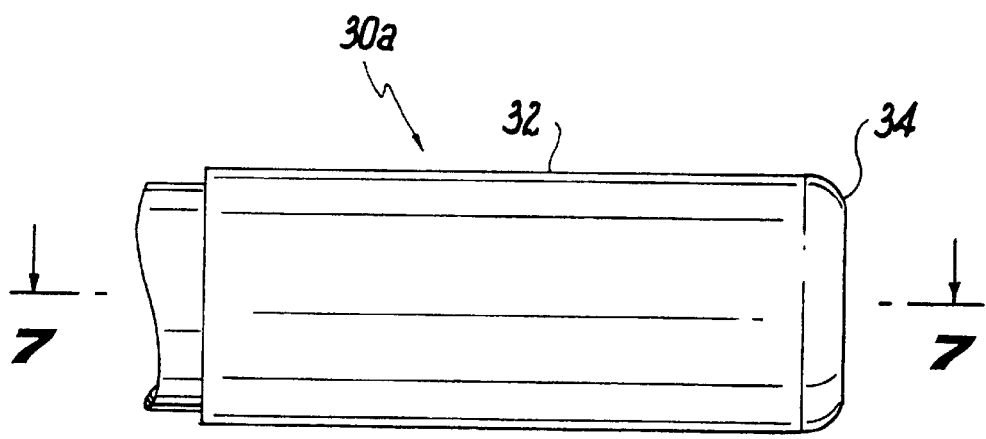
FIG. 6 is a side elevation of the present catheter of FIG. 5.
Figure 7:
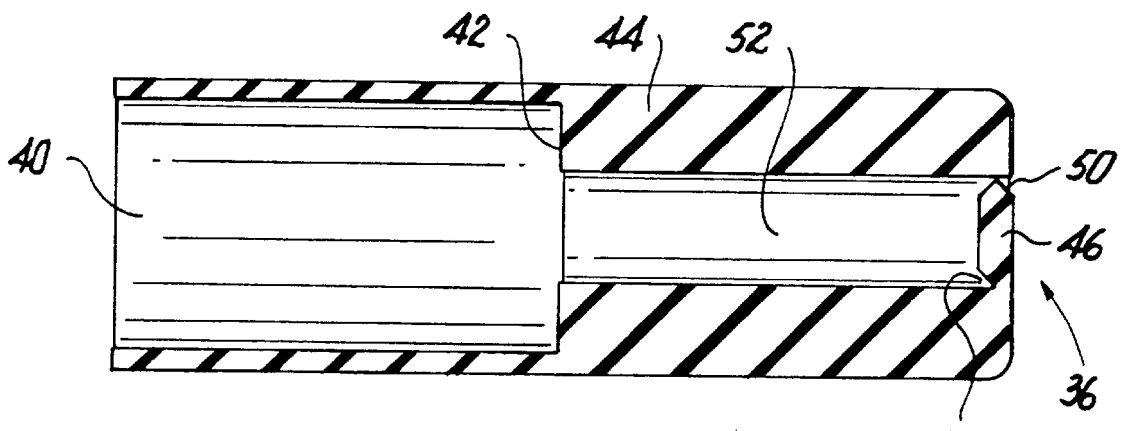
FIG. 7 is a side cross-sectional view of the catheter of FIG. 5 taken along lines 7—7 of FIG. 6.
Figure 8:
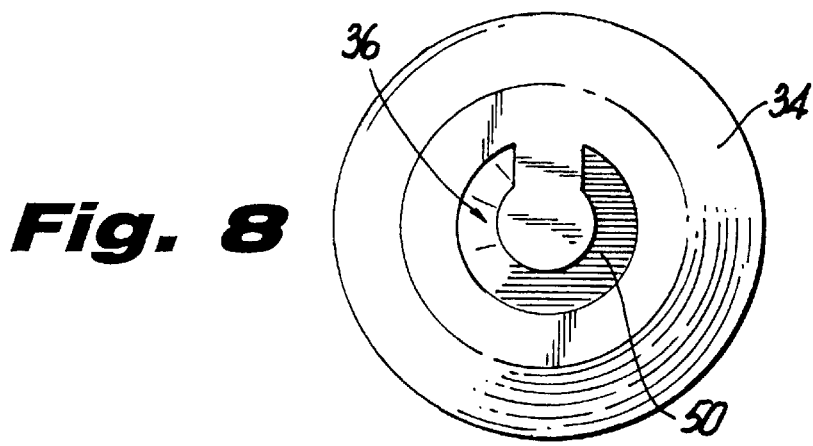
FIG. 8 is a front elevation view of the catheter of FIG. 5.

In order to facilitate manufacturing of the catheter 30, the valve 36 may be provided on a tip 30a of the catheter as shown in FIGS. 6–8. Tip 30a includes a catheter entrance 40 which accommodates the distal end of an open ended catheter which slips into tip 30a at entrance 40 and abuts against catheter abutment 42. Lumen 52 of tip 30a communicates with the lumen of the catheter as seen in FIG. 7. Catheter tip 30a includes a wall 44 having a first thickness and a reduced wall thickness 46 at valve 36, so that valve 36 is positioned exclusively within the area of reduced thickness 46 and in a plane which is at an angle to the longitudinal axis of the catheter, in this case perpendicular. In this embodiment of FIG. 7, valve 36 further includes a hinge portion 48 which facilitates opening and closing of the valve 36, and a seal 50 which seals the opening 38 at the distal end of the catheter tip. Valve 36 will flex outwardly to permit the infusion of fluids from the catheter into the vessel in which the catheter is positioned in response to increased pressure within the lumen 52, and valve 36 will flex inwardly to permit the withdrawal of fluids from the vessel and into the lumen 52.

Figure 9:
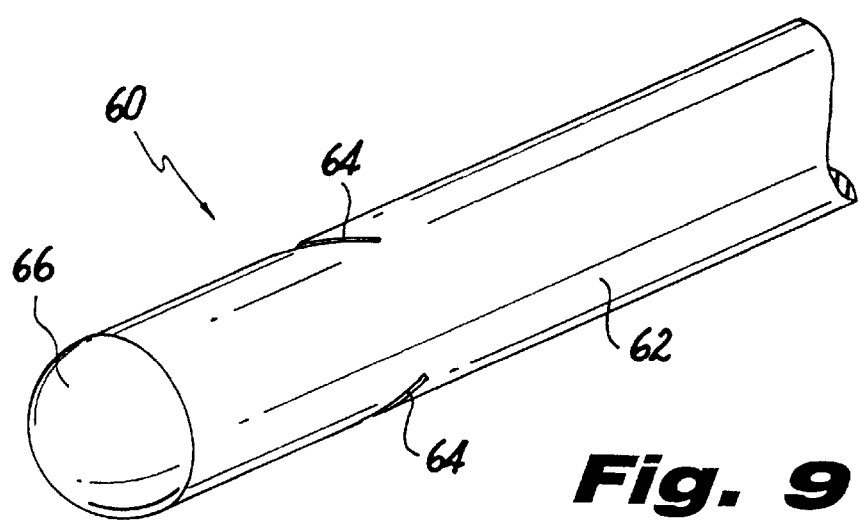
FIG. 9 is a perspective view of the present catheter according to a third embodiment.

Turning now to FIG. 9, there is illustrated an additional embodiment of the catheter 60 in which a pair of valves 64 are provided in the body 62 of the catheter 60, adjacent the closed distal end 66. Valves 64 are each positioned at an angle to the longitudinal axis of the catheter 60, and preferably at a 30° angle. Optionally, the valves 64 may be provided at angles which are opposite to each other. Preferably each such valve is positioned at an angle of approximately 30° to the longitudinal axis. Thus, in an embodiment wherein the two valves are oriented opposite to each other, the angles would be plus and minus 30 degrees relative to the longitudinal axis, respectively.

Figure 10:
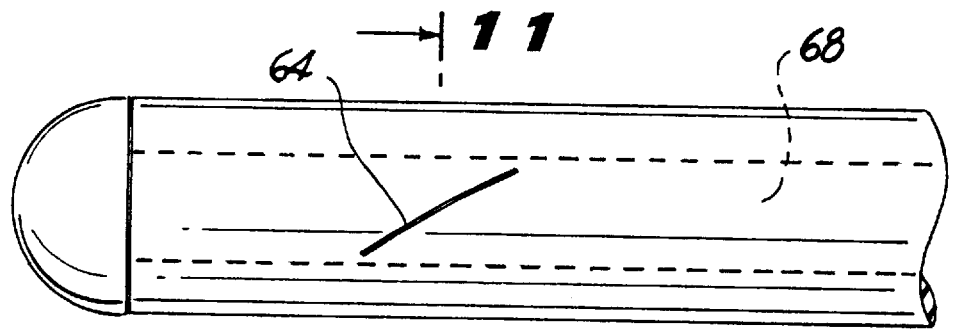
FIG. 10 is a top plan view of the present catheter of FIG. 9.
Figure 11:
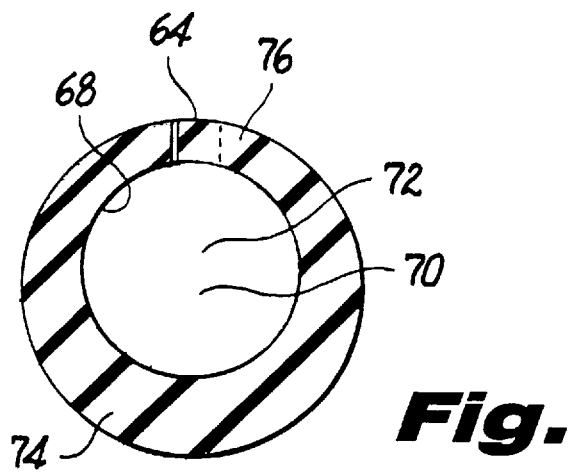
FIG. 11 is a cross-sectional view of the catheter of FIG. 9 taken along lines 11—11 of FIG. 10 showing a circular lumen.
Figure 12:
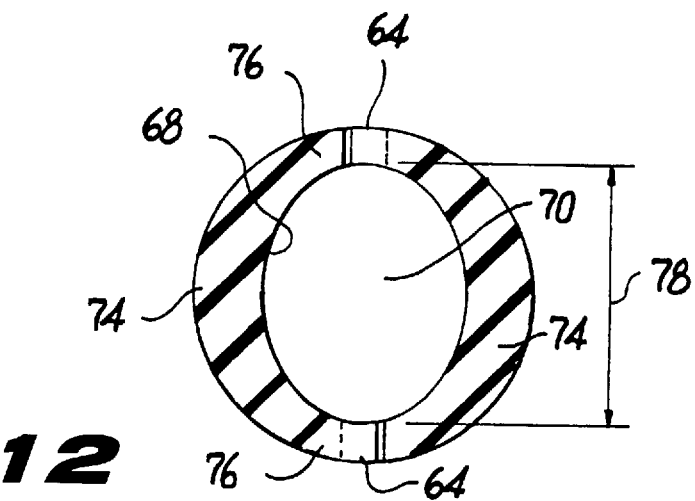
FIG. 12 is a cross-sectional view similar to FIG. 11 showing an oval lumen.

As seen in FIGS. 10–12, valve 64 is positioned exclusively within the reduced thickness portion 76 of the catheter wall 74, and is positioned at an angle to the longitudinal axis 70. The reduced wall thickness 76 is a result, as seen in FIG. 11, of extruding the catheter tubing so as to have a lumen 68 which is offset from the longitudinal axis 70 of the catheter 60. In the embodiment shown in FIG. 11, lumen 68 has a longitudinal axis 72 which is offset from the longitudinal axis 70 of the catheter 60. Wall 74 has a greater thickness than reduced thickness portion 76, and valve 64 is positioned exclusively within the reduced thickness portion 76.

FIG. 12 illustrates a further manner of extruding the catheter 60 in order to provide for the positioning of valves 64 in the reduced thickness portion 76. In this embodiment, the lumen 68 has an oval cross-section, such that its longitudinal axis is aligned with longitudinal axis 70 of the catheter 60. The reduced thickness portions 76 are located at the ends of the major axis 78 of the oval shaped lumen 68, and valves 64 are provided at the end of the major axis 78.

Figure 13:
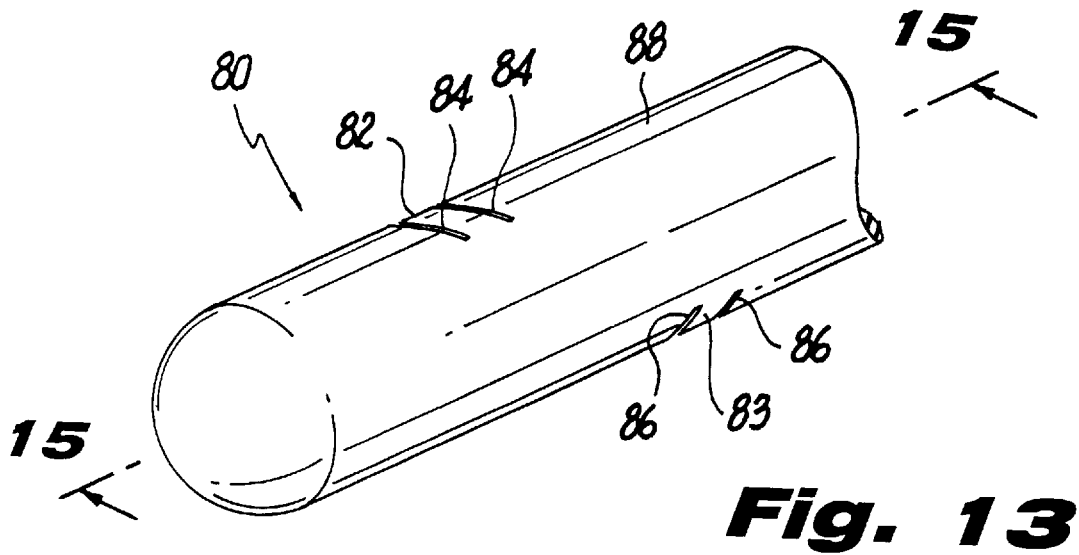
FIG. 13 is a perspective view of the present catheter according to a fourth embodiment.
Figure 14:
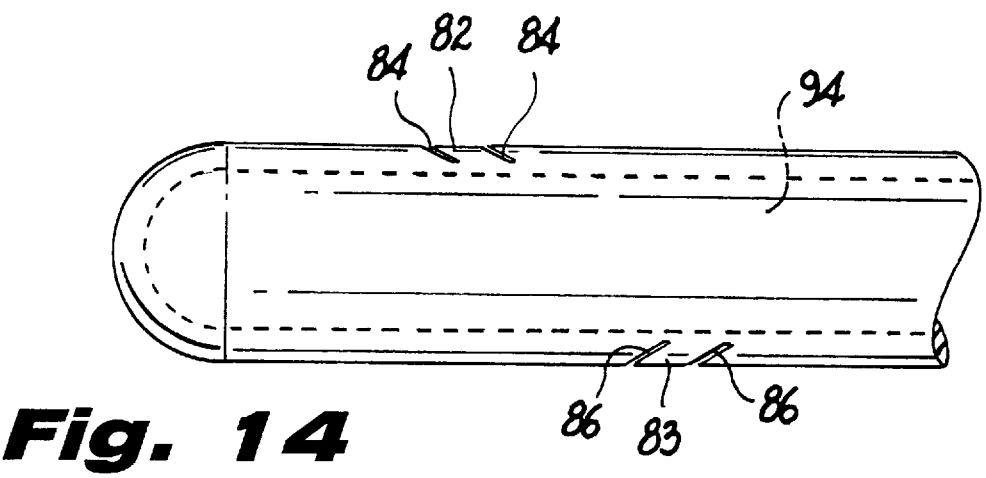
FIG. 14 is a side elevation view of the catheter of FIG. 13.
Figure 15:
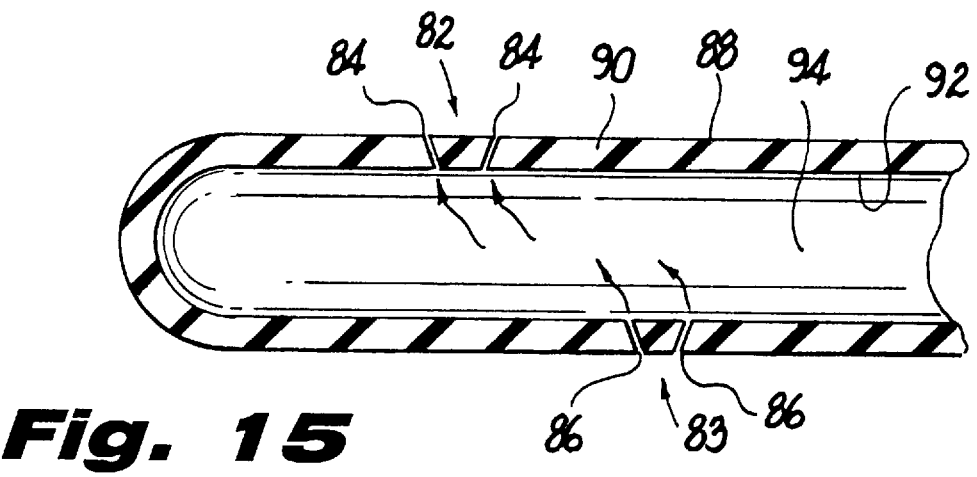
FIG. 15 is a cross-sectional view of a catheter similar to FIG. 13, except that the two slits of each valve lie in planes which intersect.

FIGS. 13–15 illustrate further embodiments of the catheter 80, in which the valves 82, 83 comprise a pair of slits 84, 84 and 86, 86. In the embodiment of FIGS. 13 and 14, the slits of each pair are placed side by side and the planes of the slits of each pair are substantially parallel. Ingress and egress of fluids occur through both valves 82, 83.

The embodiment of FIG. 15 is similar to FIGS. 13 and 14 in that each valve 82'83' has a pair of slits 84', 84', 86', 86', however, the planes of the slits of each pair intersect In this embodiment, as best seen in FIG. 15, the slits 84' are positioned side by side, spaced equidistantly along their lengths, and are cut at an angle from the outer surface 88' through wall 90' to inner surface 92' such that one of the slits 84' is cut in the direction towards the other slit 84'. Slits 84' intersect interiorly within the catheter 80 within lumen 94. When cut in this manner, valve 82' opens outwardly in response to increased pressure in the lumen 94 to permit the infusion of fluids from the lumen 94 of the catheter into the vessel in which the catheter is positioned.

As further seen in FIG. 15, slits 86' of valve 83' are cut at an angle from the outer surface 88' to the inner surface 92' through wall 90' away from each other, are positioned side by side, and spaced equidistantly along their lengths. As can be seen from FIG. 15, slits 86 will intersect exteriorly to the catheter 80. This valve opens inwardly in response to decreased pressure in the lumen 94 of the catheter 80 to permit the withdrawal or aspiration of fluids from the vessel into the catheter.

In addition, it can be seen in FIG. 15 that increased pressure in lumen 94 will force valve 83' outwardly against wall 90, further sealing valve 83' to facilitate infusion through valve 82'. Likewise, decreased pressure in lumen 94 forces valve 82' inwardly against wall 90, further sealing valve 82' to facilitate aspiration through valve 83.

FIGS. 16–18 illustrate another alternate embodiment in which a separate valve assembly 100 is mounted e.g., by insert molding, on the tip of catheter 101 to form the catheter for insertion into the body. Valve assembly 100 includes a reduced thickness area 102 around the entire circumference. Nose 104 is configured for easier penetration, is glued to the valve assembly, and seals the distal end of the catheter and assembly 100. As shown, the reduced thickness area 102 is formed by reducing the thickness of wall 105, thereby maintaining the diameter of lumen 106 constant so as not to effect flow. Note that walls 120a–120d are slightly radiused with portions 107a–d of increased wall thickness to increase stability. The transition areas 108, 109 preferably slope at an angle of about 8 to about 12 degrees to maintain stability of the catheter. A pair of diametrically opposed slits 110, 112 are angled with respect to the longitudinal axis (illustratively at an angle of about 24 degrees) and function as described above with respect to the embodiment of FIG. 1. Thus, slit valves 110, 112 open into eye-shaped openings as shown in FIG. 18A.

Length L between nose 104 and transition 108 is selected to optimize valve performance and preferably in a 9 French catheter ranges from about 0.1 to about 0.2 inches and more preferably about 0.144 inches.

Figure 19:
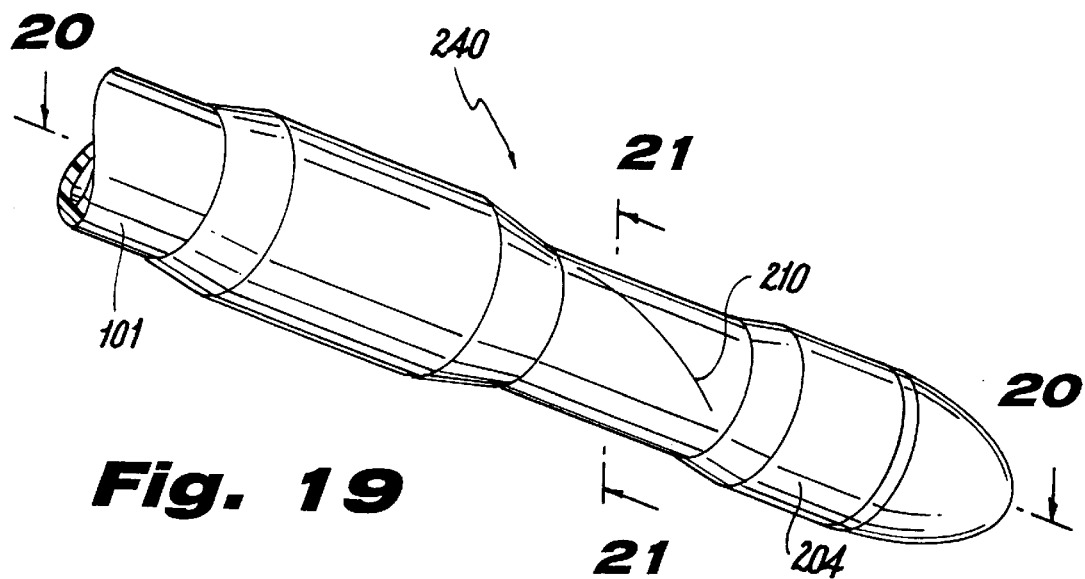
FIG. 19 is a perspective view of the present catheter according to a sixth embodiment.
Figure 20:
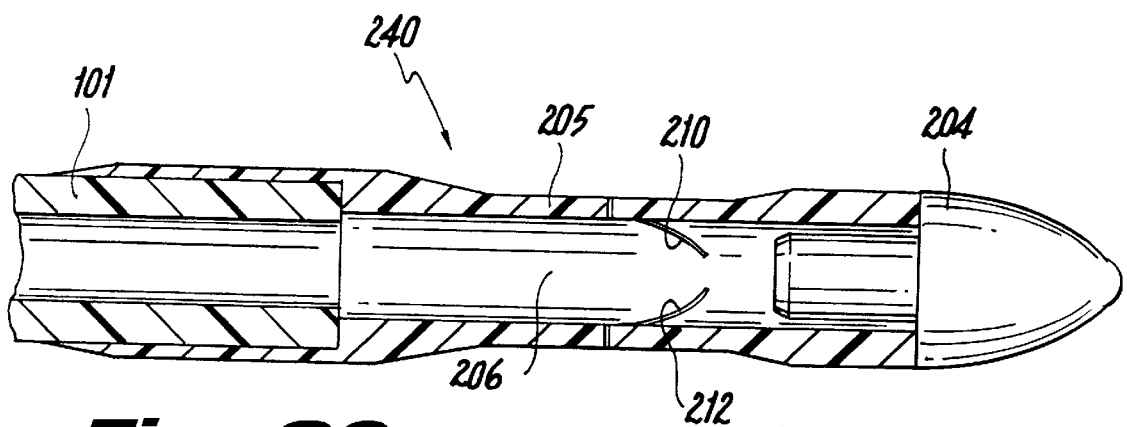
FIG. 20 is a side cross-sectional view of the catheter of FIG. 19 taken along lines 20—20 of FIG. 19.
Figure 21:
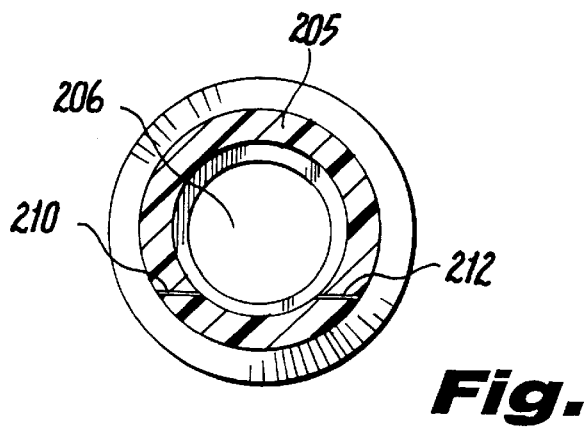
FIG. 21 is a cross-sectional view of the catheter of FIG. 19 taken along lines 21—21 of FIG. 19.

Valve assembly 240 illustrated in FIGS. 19–21 is identical to valve assembly 100 of FIGS. 16–18 except that the reduced thickness area 202 is circular in cross section. As shown, area 202 is formed by reducing the thickness of wall 205 without effecting the internal diameter of lumen 206. Nose 204 is affixed in the same manner as nose 104. Slits 210, 212 are illustratively angled at about 24 degrees. As with the aforementioned embodiments, other angles are contemplated.

As noted above, the combination of an angled slit disposed on a region of reduced thickness results in a larger opening. FIG. 18A illustrates by way of example the resulting eye shaped opening O which can be achieved.

While the catheter has been particularly shown and described with reference to the illustrated embodiments, it will be understood by those skilled in the art that various modifications and changes in form and detail may be made therein without departing from the scope and spirit of the novel aspects of the above-described catheter. Accordingly, modifications such as those suggested above, but not limited thereto, are to be considered within the scope of the appended claims.

What is claimed is:

1. A catheter comprising:
    an elongated, flexible tube having an open end and a closed end and being constructed of surgical grade material, the tube having an outer surface and a lumen extending the length of the tube so as to define an inner surface, the inner and outer surfaces defining a wall of the tube;
    a portion of the tube having a reduced thickness with respect to the remainder of the tube; and
    at least one valve positioned exclusively within the portion of reduced thickness so as to communicate the lumen with an exterior of the tube, the valve being oriented in a plane which is at an angle to a longitudinal axis of the tube.

2. A catheter according to claim 1, wherein the lumen is tubular and is defined by a circular cross-section, a longitudinal axis of the lumen being offset and parallel to the longitudinal axis of the tube to define the portion of reduced thickness in the wall.

3. A catheter according to claim 1, wherein the lumen is defined by an oval cross-section, a longitudinal axis of the lumen being aligned with the longitudinal axis of the tube, such that the major axis of the oval defines portions of reduced thickness in the wall of the tube.

4. A catheter according to claim 1, wherein the reduced thickness portion of the tube is circular in cross section.

5. A catheter according to claim 1, wherein the valve comprises a slit valve which is oriented at an angle of approximately 30° to the longitudinal axis.

6. A catheter according to claim 5, further comprising a second slit valve which is oriented at an angle of approximately 150° to the longitudinal axis.

7. A catheter according to claim 3, further comprising a second valve, wherein the first valve is positioned at one end of the major axis of the oval cross-section and the second valve is positioned at a second end of the major axis.

8. A catheter according to claim 7, wherein the first and second valves are slit valves, the first valve being oriented at an angle of approximately 30° to the longitudinal axis and the second valve being oriented in a plane which is at an angle of approximately 150° to the longitudinal axis.

9. A catheter according to claim 1, wherein the portion of reduced thickness includes at least one planar region adjacent the closed end of the tube, the lumen having a constant diameter along its length.

10. A catheter according to claim 9, wherein the valve comprises a slit valve which is oriented at an angle of approximately 30° to the longitudinal axis.

11. A catheter according to claim 10, further comprising a second slit valve which is oriented at an angle of approximately 30° to the longitudinal axis.

12. A catheter according to claim 11, wherein the first valve is diametrically opposite the second valve.

13. A catheter according to claim 1, wherein the portion of reduced thickness is adjacent the closed end of the tube, such that the lumen has a constant diameter along its length.

14. A catheter according to claim 13, wherein the valve comprises a slit valve which is oriented in a plane which is at an angle of approximately 30° to the longitudinal axis.

15. A catheter according to claim 14, further comprising a second slit valve which is oriented in a plane which is at an angle of approximately 30° to the longitudinal axis.

16. A catheter according to claim 15, wherein the first valve is diametrically opposite the second valve.

17. A catheter according to claim 1, wherein the distal portion of the tube is attached to the remainder of the tube.

18. A catheter according to claim 17, further comprising an end cap attached to the distalmost end portion of the distal portion of the tube to form the closed end.

19. A catheter comprising:

an elongated, flexible tube having a proximal end and a distal end and being constructed of surgical grade material, the tube having an outer surface defining a first diameter and a lumen extending the length of the tube so as to define an inner surface, the inner surface and the outer surface defining a wall of the tube;

a portion of the tube adjacent the distal end having an outer surface defining a second diameter, the first diameter being greater than the second diameter; and at least one valve positioned in the portion having the second diameter so as to communicate the lumen with an exterior of the tube, the valve being oriented in a plane which is at an angle to a longitudinal axis of the tube.

20. A catheter according to claim 19, wherein the valve comprises a slit valve which is oriented in a plane which is at an angle of approximately 30° to the longitudinal axis.

21. A catheter according to claim 20, further comprising a second slit valve which is oriented in a plane which is at an angle of approximately 150° to the longitudinal axis.

22. A catheter according to claim 21, wherein the first valve is diametrically opposite the second valve.

23. A catheter comprising:

an elongated, flexible tube having at least one open end and being constructed of surgical grade material, the tube having an outer surface, a lumen extending along the length of the tube and defining an inner surface, the inner and outer surfaces of the tube defining a wall of the tube, the lumen having a longitudinal axis which is offset and parallel to a longitudinal axis of the tube such that a portion of the wall of the tube has a reduced thickness along the length of the tube, and at least one slit valve extending exclusively through the portion of reduced thickness of the wall to communicate the lumen with an exterior of the tube, the slit valve being oriented in a plane which is at an angle to the longitudinal axis of the tube and the lumen.

* * * * *